(12) United States Patent
Murphy (10) Patent No.: US 6,599,241 B1
(45) Date of Patent: Jul. 29, 2003

(54) DIAGNOSTIC SYSTEM AND APPARATUS

(75) Inventor: Graham Francis Murphy, Alresford (GB)

(73) Assignee: Remote Diagnostic technologies Limited, Basingstoke (GB)

( * ) Notice: Subject to any disclaimer, the term of this patent is extended or adjusted under 35 U.S.C. 154(b) by 0 days.

(21) Appl. No.: 09/568,708

(22) Filed: May 11, 2000

(30) Foreign Application Priority Data

May 11, 1999  (GB) .............................................. 9910938

(51) Int. Cl.[7] .......................... A61B 5/00; G06F 19/00; G09G 5/00
(52) U.S. Cl. ....................... 600/300; 128/903; 128/904; 345/733; 345/716; 702/19
(58) Field of Search ................................ 345/716, 719, 345/733, 1.1; 725/105; 600/300–301, 549, 500–516, 529, 532, 481, 322–324; 128/903, 904, 920–925; 705/2–4; 702/19; 434/262; 709/200

(56) References Cited

U.S. PATENT DOCUMENTS

| | | | | |
|---|---|---|---|---|
| 5,544,649 A | * | 8/1996 | David et al. ................. | 600/300 |
| 5,544,661 A | | 8/1996 | Davis et al. | |
| 5,553,609 A | * | 9/1996 | Chen et al. .................. | 600/300 |
| 5,586,556 A | | 12/1996 | Spivey et al. | |
| 5,704,364 A | * | 1/1998 | Saltzstein et al. ........... | 600/300 |
| 5,713,350 A | * | 2/1998 | Yokota et al. ............... | 600/300 |
| 5,802,494 A | * | 9/1998 | Kuno ........................... | 705/2 |
| 6,014,432 A | * | 1/2000 | Modney ................. | 379/106.02 |
| 6,283,923 B1 | * | 9/2001 | Finkelstein et al. ......... | 379/532 |
| 6,290,646 B1 | * | 9/2001 | Cosentino et al. .......... | 600/300 |

FOREIGN PATENT DOCUMENTS

| | | |
|---|---|---|
| JP | 7095556 | 4/1995 |
| JP | 10234682 | 9/1998 |
| WO | WO 98/40009 | 9/1998 |

* cited by examiner

Primary Examiner—Max F. Hindenburg
Assistant Examiner—Michael Astorino
(74) Attorney, Agent, or Firm—RatnerPrestia (57) ABSTRACT

Medical sensors (1 to 4) are connected to a processor (6) comprising a PC and modems (14 and 16). The modems are connected to respective low power transmitter/receivers (18 and 20). The transmitter/receivers (18, 20) communicate with corresponding receiver/transmitters (18', 20') connected to a long range transmitter/receiver such as a satellite communications link (26). The communications links have a narrow bandwidth. An operator of the apparatus has a hands free headset comprising a microphone (7) and earpieces (8), and has a head-up display (10). An electronic camera (9) is provided. Medical data from the sensors (1–4) and images from the camera (9) and voice signals from the microphone (7) are processed by the processor (6), and transmitted to a remote location (B), for use by a medical practitioner having a corresponding processor and display to diagnose the condition of a patient. The medical practitioner can talk to the operator to advise on the condition and treatment of the patient.

The diagnostic apparatus and the response center (24) store respective identical libraries of context sensitive help-screens including, for example, graphical images illustrating the operation of the apparatus. Images produced by the camera (9) are stored at both the apparatus (6) and the response center (24). The response center (24) can select help screens and/or images (once stored) and cause them to be displayed on the diagnostic apparatus. The response center (24) can send annotations of help screens and/or images to the diagnostic apparatus.

36 Claims, 3 Drawing Sheets

DIAGNOSTIC SYSTEM AND APPARATUS

BACKGROUND OF THE INVENTION

1. Field of the Invention

The present invention relates to a diagnostic systems and also to diagnostic apparatus for use in the system.

A preferred embodiment of the invention as described herein is for use in aircraft for the diagnosis of medical emergencies, on aircraft in flight, of humans. However, the invention is not limited to that. The medical diagnostic equipment may be used on other vehicles, e.g. ships, and may be useful on land especially in locations remote from medical help. The invention may also be applied to the diagnosis of faults in machines, for example aircraft, and electronic equipment.

2. Description of the Prior Art

PCT/GB98/00613, WO-A-98/40009 discloses such a diagnostic apparatus. The apparatus is intended for use by non-expert people (i.e. people who have little or no medical training) in locations remote from skilled medical assistance. For example the apparatus may be used on an aircraft by flight crew who may have had some training but who seldom use the equipment and then only in conditions of a suspected medical emergency. The apparatus is linked by narrow-band communications channels to a response centre where expert medical advice is available.

SUMMARY OF THE INVENTION

It is desired to provide diagnostic apparatus which is easy to use by people who have little, or even no, training in its use and who have little or no expertise in the body being diagnosed, for example no medical expertise in the case that the body being diagnosed is a human.

The apparatus of WO 98/40009 has narrow-band communications links with a remote response centre. It is thus necessary to avoid transmitting large amounts of data between the diagnostic apparatus and the response centre.

According to one aspect of the invention, there is provided a diagnostic system comprising:

a diagnostic apparatus having at least one diagnostic sensor and a display for displaying an image;

a complementary apparatus having a display for displaying an image;

a communications system by which the diagnostic apparatus and the complementary apparatus communicate;

the diagnostic apparatus and the complementary apparatus being arranged to display the same image; and the complementary apparatus having means for annotating the displayed image and for transmitting, to the diagnostic apparatus, data representing the annotation, the diagnostic apparatus being arranged to display the annotation on the image displayed thereat.

The image may be an image (a help screen) illustrating the operation of the apparatus or an image of the person undergoing diagnosis. An expert at the complementary apparatus which displays the same image annotates the image at the diagnostic apparatus to assist the users. Thus inexpert users can be guided by the expert.

The communication system may provide a narrow-band width and thus a low data rate. Bandwidth is preserved because only data representing the annotation is transferred from the complementary apparatus to the diagnostic apparatus (not the image together with the annotation).

Preferably, the said data representing an annotation comprises a file containing information representing the annotation, the diagnostic apparatus being arranged to display the annotation represented in the file. Alternatively, the said data representing an annotation comprises commands and variables defining the annotation, the diagnostic apparatus being arranged to recreate the annotation therefrom.

In a preferred embodiment, the diagnostic apparatus and the complementary apparatus each have stores for storing images, the diagnostic apparatus storing a set of a plurality of images and the complementary apparatus storing an identical set and the said images have identifiers, and the identifier of an image to be displayed at one of the diagnostic apparatus and the complementary apparatus is transmitted to the other to cause it to display the same image stored in the store thereof. Thus images may be displayed and selected (and annotated) without the need to transmit large amounts of data between the diagnostic apparatus and the complementary apparatus.

Another aspect of the invention provides a diagnostic apparatus for use with a complementary apparatus having a display for displaying an image, the diagnostic apparatus having:

at least one diagnostic sensor and a display for displaying an image;

a communication system by which the diagnostic apparatus and the complementary apparatus communicate;

the diagnostic apparatus and the complementary apparatus being arranged to display the same image;

the diagnostic apparatus being arranged to receive from the complementary apparatus, via the communication system, an annotation of the image and to display the annotation on the image displayed thereat.

In a preferred embodiment of the invention, most actions taken at the diagnostic apparatus are replicated at the complementary apparatus. All images displayed at the diagnostic apparatus are displayed at the complementary apparatus. The ability of an expert at the complementary apparatus to see the images and the manner in which the apparatus is used and to annotate images allows the expert to use annotations to guide the users.

In a most preferred embodiment the users communicate with the expert via a voice channel. They can thus ask for guidance and the expert can provide such guidance by voice and by annotation.

According to another aspect of the invention, there is provided a diagnostic system comprising: a diagnostic apparatus having at least one diagnostic sensor and a display for displaying an image; a complementary apparatus having a display for displaying an image; a communication system by which the diagnostic apparatus and the complementary apparatus communicate; the diagnostic apparatus and the complementary apparatus being arranged to display the same image; wherein the diagnostic apparatus and the complementary apparatus each have stores for storing images, the diagnostic apparatus storing a set of a plurality of images and the complementary apparatus storing an identical set and wherein the said images have identifiers, and the identifier of an image to be displayed at one of the diagnostic apparatus and the complementary apparatus is transmitted to the other to cause it to display the same image stored in the store thereof.

Thus bandwidth is preserved because identical images sets are stored at the diagnostic apparatus and at the complementary apparatus and the same images are selected for display by transmitting the identifiers avoiding the need to transmit whole images.

In a preferred embodiment, the images stored at the diagnostic apparatus include images which are displayable at the diagnostic apparatus only in response to a command from the complementary apparatus. For example such images may illustrate medical procedures and which should be made available to the users of the diagnostic apparatus only under the supervision of the expert operating the complementary apparatus.

According to a further aspect of the present invention, there is provided a diagnostic apparatus comprising:

means for sensing data of a body,
communication means for transmitting sensed data to a remote location and for receiving control data from the remote location,
display means,
processing means to which the sensing means, communication means and display means are connected to form an integrated system,
the processing means being arranged to:
 a) control the sensing means;
 b) process the sensed data; and
 c) control the communication means;
the processing means storing a set of images each image having a unique identifier, the processing means being responsive to a command from the remote location to select and display a stored image identified by the command.

According to another aspect of the present invention, there is provided a diagnostic system comprising:

diagnostic apparatus according to said one aspect of the invention: and
a device at the remote location comprising communication means for receiving sensed data from the diagnostic apparatus, a display and a processor, the processor of the device storing a set of images identical to the said set of images stored by the said processing means.

Because the images are stored in the diagnostic apparatus and an image is selected for display by a command identifying the image, only the command and identifier need be transmitted, reducing the amount of data to be transmitted. At least some of the images include context sensitive instructions. The appropriate image can be selected by an operator at the remote location to assist the user.

In a preferred embodiment of the invention, the processing means is responsive to an image annotation, together with the identifier of the image to be annotated, received from the remote location to combine the annotation with the identified image stored by the processing means and to display the annotated image. By transmitting from the remote location only annotations and not the combined image and annotation, the amount of data transmitted is minimised. In a most preferred embodiment, the apparatus and the remote location run the same image processing software which includes annotation tools. Then it is necessary to transmit only variables identifying the annotation tools minimising the data to be transmitted. The variables may be transmitted in a file or in near real time as variables per se.

Zoom and pan variables may also be provided from the remote location to the diagnostic apparatus. Preferably the zoom and pan variables are transmitted as such and not in files. They enable the remote location to guide the operator of the diagnostic apparatus in near real time by emphasising portions of the images displayed at the diagnostic apparatus whilst minimising the data transmitted.

The images mentioned above may be graphics which are used for example as help screens aiding the operator of the diagnostic apparatus and or images produced by a camera of the diagnostic apparatus.

In accordance with a yet further aspect of the invention, there is provided a diagnostic system comprising:

a diagnostic apparatus having at least one diagnostic sensor and a display for displaying an image;
a complementary apparatus having a display for displaying an image;
a communication system by which the diagnostic apparatus and the complementary apparatus communicate one with the other;
the diagnostic apparatus being arranged to perform a predetermined plurality of actions; the diagnostic apparatus and the complementary apparatus being arranged so that the complementary apparatus replicates the said actions.

Thus an expert at the complementary apparatus is able to monitor all the predetermined actions taken at the diagnostic apparatus.

BRIEF DESCRIPTION OF THE DRAWINGS

For a better understanding of the present invention reference will now be made by way of example to the accompanying drawings, in which.

DESCRIPTION OF ILLUSTRATIVE EMBODIMENTS

The invention will be illustrated by reference to apparatus for use on an aircraft for diagnosis of human passengers (hereinafter patients). However as will be made clear, the invention is not limited to that. The apparatus allows the communication of medical diagnostic data from the aircraft A to a medical practitioner at a remote location B and for medical diagnostic advice and, if necessary, treatment advice to be transmitted from the remote location B to the aircraft. The medical data may be transmitted to one or more other locations C to obtain further advice.

The diagnostic apparatus comprises a plurality of medical sensors, including a battery powered ECG (ElectroCardioGram, also termed EKG) sensor array 1, a blood pressure sensor and pulse oximeter 3 which measures blood oxygen and pulse rate, and one or more other sensors such as a temperature sensor 2 and a capnometer 4. In the example shown in FIG. 1, the temperature sensor 2 is an infra-red ear thermometer. The capnometer 4 measures end tidal $CO_2$, respiration rate and other functions. The ECG sensor array 1 is preferably a 12 lead array but could be a 4 lead array or be any other suitable ECG array. The ECG sensor array 1 produces many signals together having relatively high data rate. The other sensors have relatively low data rate (compared to the ECG array 1).

In a most preferred embodiment of the invention, the sensors comprise a 12 lead ECG sensor array 1, a blood pressure sensor and a pulse oximeter 3, a temperature sensor 2 and a capnometer 4 which are together considered by some experts to be essential for the reliable diagnosis of the seriousness of medical conditions of airline passengers.

Figure 1:
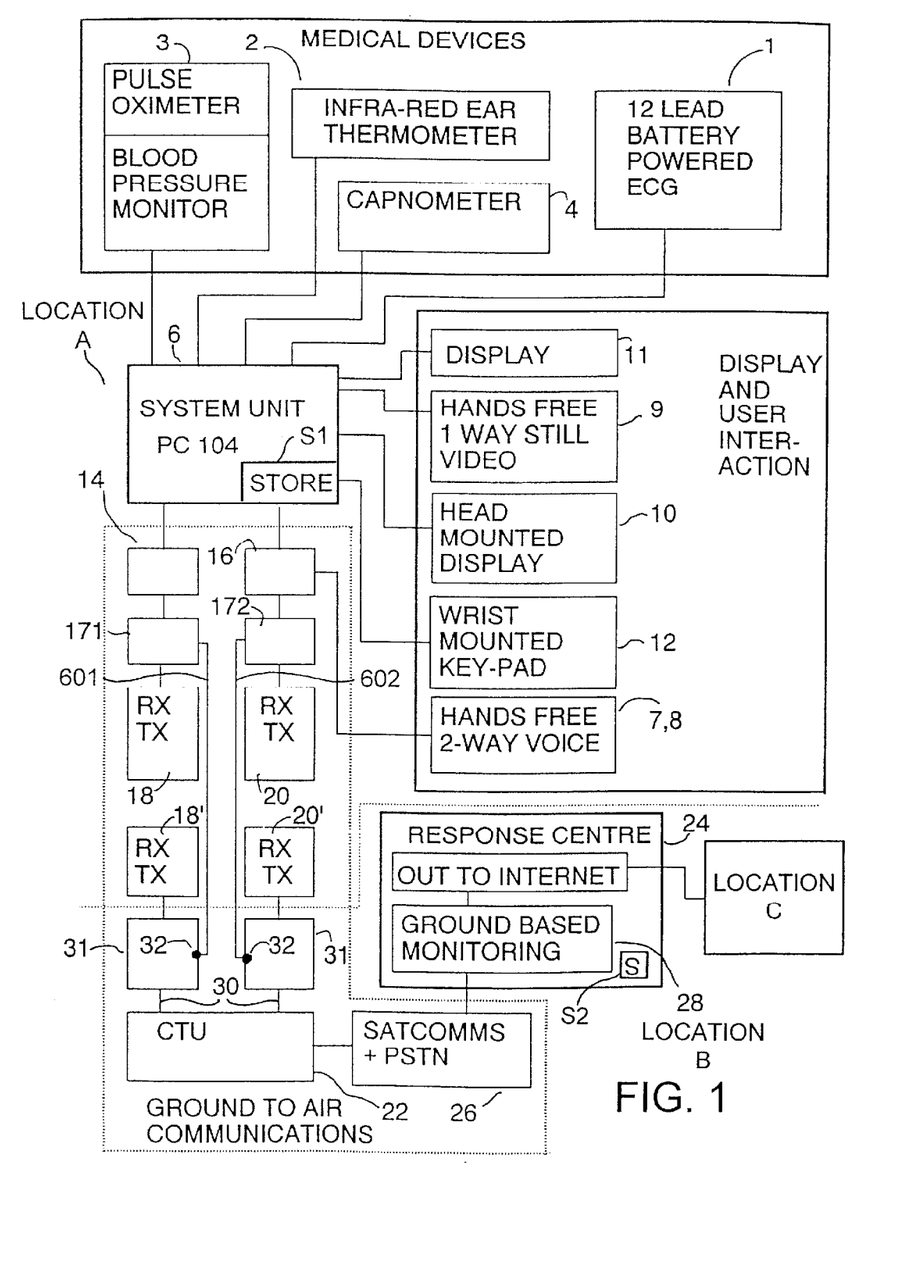
FIG. 1 is a system block diagram of an illustrative medical diagnostic apparatus for use on an aircraft, and a ground-based response centre and a communications system.

The medical sensors are connected to a computer 6 comprising, in this example, a PC 104 processor (which is a known, standard, processor) having a Pentium (Trade Mark) 133 Mhz processor, 32 Mb RAM, 1 Gb hard drive represented in FIG. 1 as a store S1, a video controller for a display device, 6 ports and a centralized power supply for all equipment. The PC 104 runs for example the Microsoft Windows NT Operating system (Microsoft, Windows and NT are Registered Trade Marks).

The combined blood pressure monitor and pulse oximeter 3, the thermometer 2, the ECG array 1 and the Capnometer 4 are connected to respective inputs of the processor 6.

Also provided are: a microphone 7, a loudspeaker and/or earpiece 8, a digital camera 9, a head-up display 10, an LCD display 11, and a wrist pad 12 having keys for operating the apparatus.

The microphone 7, and earpiece 8 are preferably provided as a commercially available integral audio head-set for hands free operation. A small head-up display 10 which also provides hand free operation is also commercially available. The digital camera 9 may be wrist mounted together with the wrist pad 12 also for ease of use.

Figure 4:
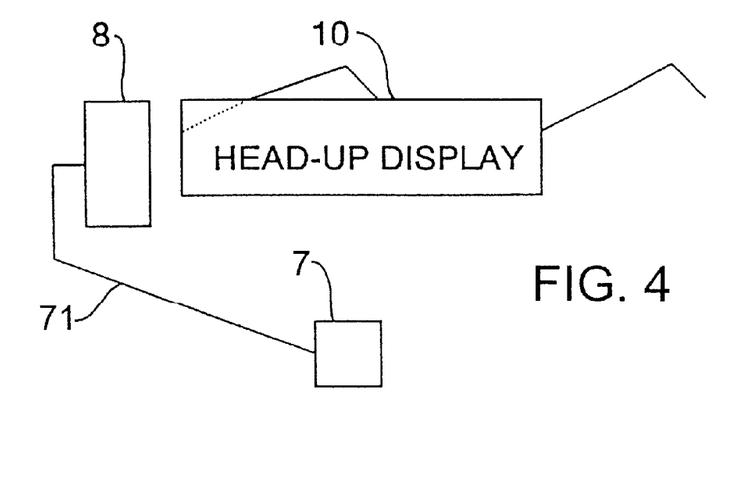
FIG. 4 is a schematic block diagram of a head-up display and audio equipment for use by the operator of the apparatus of FIG. 1.

The headset comprising the microphone 7 and the earpiece 8 for hands free operation is currently considered essential to this embodiment of the invention: the head up display 10 for hands free operation is a preferred but optional feature. Examples of the audio head set 7, 8 and head up display 10 are shown in FIG. 4. The head set comprises a single ear-piece and the microphone 7 is mounted on a boom 71 to be adjacent to the operators mouth for hands free use. The head-up display 10 in this example is mounted on a spectacle frame for hands free use. The spectacle frame may be provided by safety spectacles to protect the operator. In a most preferred embodiment a single earpiece containing a microphone is used.

Figure 5:
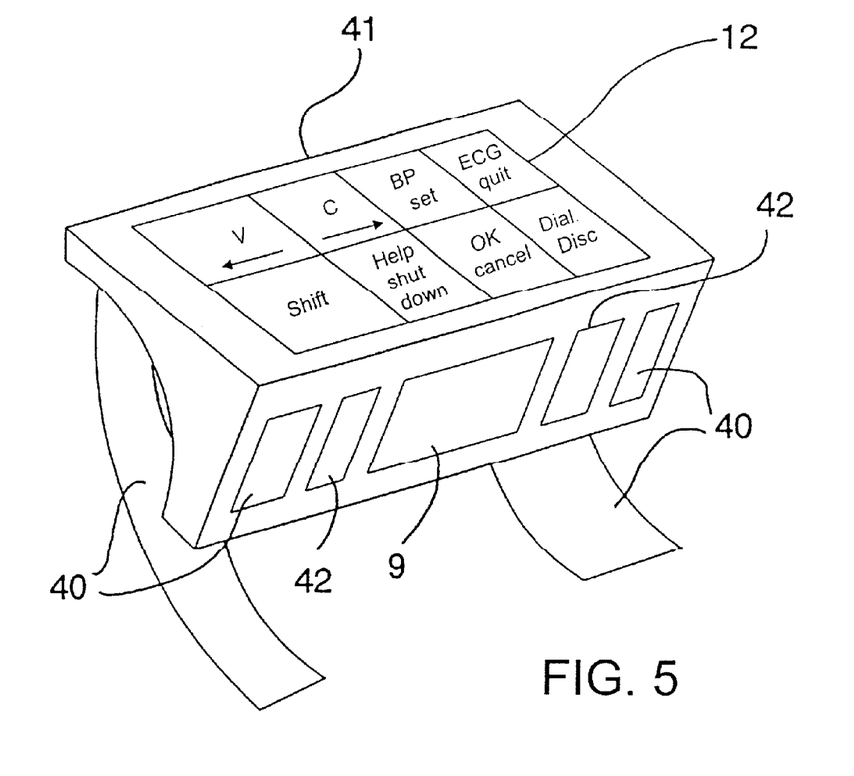
FIG. 5 is a schematic block diagram of a wrist pad for use with the apparatus of FIG. 1.

The PC 104 in this example has no keyboard. Instead the operator is provided with a key pad 12 attached to his/her wrist by a strap 40 as shown in FIG. 5. The key pad 12 has a minimum set of keys needed to operate the apparatus. In this example the keypad has 8 keys. Referring to FIG. 5 the keys comprise from top left to bottom right: a video control key V; a capnometer control key C; a blood pressure monitor control key BP; an ECG control key ECG; a shift key; a help key; an OK key; and a Dial control key for initiating auto-dial. All the keys except the shift key have a shift level as follows: Shift V is left arrow: shift C is right arrow: shift BP is set the configuration of the Blood pressure monitor: shift ECG is quit the ECG; shift help is shut down the whole system: shift OK is cancel: and shift Dial is disconnect.

In a preferred embodiment of the invention, there is no shift key. Instead there is one key for each function. That makes the apparatus easier to operate.

The digital camera 9 is preferably a digital video camera which provides moving images of the patient on the head up display 10 and the LCD display 11 to provide a viewfinder action without needing to bring the camera to the operators eye. As will be described hereinafter, a still image is "grabbed" from the video for transmission, when required, to the medical expert at the remote location. A digital stills camera could be used but is not currently preferred.

As shown by way of example in FIG. 5 the camera 9 is preferably housed in a wrist mounted housing 41 which also houses the keypad 12. The housing is shaped to match a persons wrist/forearm to which it is attached by Velcro (Registered Trade Mark) straps 40. The housing 41 also has a holder 42 (shown schematically) for holding the head-up display 10. The keypad 12, the camera 9 and the head-up display 10 have respective cables which can be difficult to handle especially when initially retrieving them from the container (described hereinafter) in which they are stored and when the operator puts the wrist-mounted housing 41 and head-up display 10 on. The present inventor has discovered that handling of the wrist-mounted housing 41, the head-up display 10 and the cables is considerably easier if the head up display 10 is initially fixed to the wrist-mounted housing 41 whilst that is retrieved from the container and whilst the housing 41 is fixed to the wrist of the operator. The head-up display 10 is then removed from the wrist mounted housing 41 and put on the operators head.

The head-up display 10 and the LCD display 11 display the medical data produced by the medical sensors 1, 2, 3 and 4 as processed by the PC 104. The head-up display 10 allows the operator to monitor the medical data. The LCD display 11 is provided to allow someone assisting the operator to monitor the data. In addition the head-up display 10 and/or the LCD display 11 are used to display operating instructions as will be discussed hereinafter.

A currently preferred embodiment omits the head up display.

An LCD display may be provided in the wrist mounted housing as a viewfinder for the camera.

The apparatus as so far described is coupled by two interfaces 14, 171; 16, 172 to two communications channels as will be described hereinafter. The interfaces provide in known manner isolation of the diagnostic apparatus and the aircraft's' communication network from each other. One interface 14, 171 comprises a modem 14, which is used to transmit the medical data from the sensors 1 to 4 as processed by the PC 104. The processor 6 autodials via the modem 14 when so instructed by the operator to establish the communications link with the response centre 24. Modem 14 provides the sensor data to one of the communications channels. In this case the complete ECG data files, and still images from camera 9 are transmitted in batches. The modem 14 also provides transmission of the medical data from the other sensors 2, 3 and 4 in near real time. The processor encodes the sensor data in TCP/IP format and the medical data from the ECG array 1 and images from the camera 9 are transmitted as files using the FTP mode, in this example. Other modes of transmission are possible.

The other interface 16, 172 is an audio interface controlled by the processor for providing two-way voice communication to and from the audio head-set 8 and 7. The processor 6 auto-dials, when so instructed by the operator, via the audio interface 16, 172 to establish the communications link. The interface could include a modem 16 which provides the auto-dial function under the control of the processor 6. In this example, the interfaces 14, 171, 16, 172 are connected to respective wireless transmitter/receivers 18 and 20 and also to telephone cords 601 and 602. The transmitter/receivers 18 and 20 are preferably cordless telephones. An example is a CT2 cordless telephone. CT2 is a signal transmission/reception standard known from MPT 1334 and BS 6833. CT2 conforms to the common air interface and is a digital time division multiplex TDM system. The CT2 standard is approved for use in civil aircraft. It provides low-power, low range signals. However, other standards may be used such as CDMA which uses spread spectrum techniques. Most preferably cordless phones complying with the DECT standard are used at reduced power. The transmitter/receivers 18 and 20 communicate with corresponding cordless base stations 18', 20' coupled to a long range RF transmitter/receiver 26. In this example for use on aircraft, the long range transmitter/receiver 26 is part of communications satellite link (satcomms link) to a ground station 24 and the cordless base stations 18' and 20' are coupled to the aircraft's CTU (Cabin Telephone Unit) 22 which interfaces with the satcomms link and PSTN 26.

Some aircraft are equipped with an internal wired telephone network 30 with, for example, telephones 31 in the backs of seats or at least on bulkheads within the passenger areas in the aircraft. This allows the passengers and crew to make telephone calls via the CTU 22 and the satcomms link and PSTN 26. The telephones are equipped with RJ45 telephone sockets 32 to allow other telephonic equipment to be connected to them. The cords 601 and 602 are provided for connecting to such sockets 32 for connection via the CTU 22 to the satcomms link and PSTN 26. Cordless base stations 18' 20' for use with the cordless phones would be plugged into the RJ45 sockets for coupling the cordless phones to the CTU 22. The interfaces 14, 171 and 16, 172 include circuits 171 and 172 which, in co-operation with the PC 104, automatically sense whether the cordless phones or the wired connections are in operation and route the signals to whichever is operative. The circuits 171 and 172 use high input impedance sensors to sense line voltage on the cords 601 and 602 without reducing the line voltage which would activate a connection. If a line voltage is detected a switch couples the modem 14 and the voice channel 16, 7, 8 to the CTU 22 via the cords 601 and 602. If no line voltage is detected the cordless phones are actuated by default. Thus the operator simply plugs either the cords 601 and 602 or the cordless base stations 18', 20' into the aircraft's wired telephone network 30 and the operator does not need to take any other action to activate the communications links except for initiating auto-dial. This allows use of the apparatus at the seat of the patient.

Figure 2:
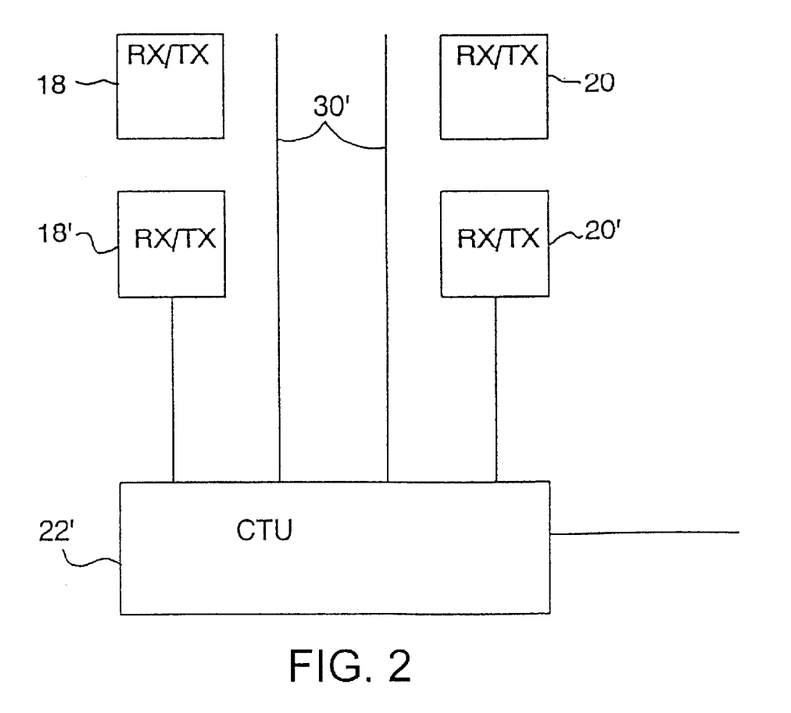
FIGS. 2 and 3 are schematic block diagrams of modifications of the apparatus of FIG. 1.
Figure 3:
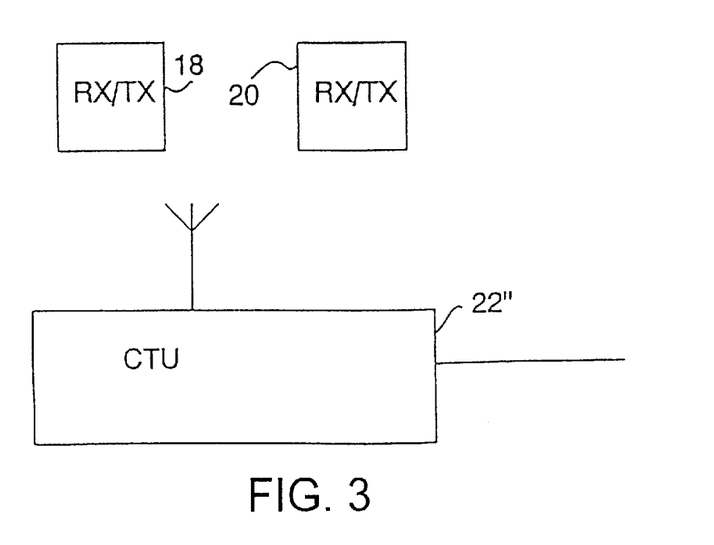

Various modifications which may be made to the foregoing arrangements are illustrated in FIGS. 2 and 3. Referring to FIG. 2, the diagnostic apparatus has two cordless transmitter/receivers 18 and 20. As schematically shown in the example of FIG. 2, an aircraft is equipped with a wired telephone system 30' connected to the CTU 22' for use by passengers and crew for two way telephone communication via the satcomms link and PSTN 26. Passengers have corded phones not shown. In this example of the invention two ports of the CTU 22' have cordless base stations 18', 20' wired to them. The base stations 18' and 20' or the channels thereof may be provided by a single transmission/reception card which slots into a spare circuit board slot in the CTU 22'. Thus the apparatus can be used anywhere on the aircraft without the need for corded connections As shown in the example of FIG. 3, some aircraft may be equipped with a wireless CTU 22". In this case the transmitter/receivers 18, 20 communicate directly with the CTU 22".

In the examples given above, two telephone channels are used which are standard telephonic voice channels available on an aircraft. The medical data, image signals and audio signals are multiplexed onto the channels with division of voice to one channel and data to the other.

The processor 6 is arranged, once operation is initiated, to automatically auto dial the telephone numbers of devices at the remote location B corresponding to the interfaces 14, 16, 171, 172 at the apparatus to establish the communications links. The numbers are auto dialled sequentially. The operator needs only to initiate auto dialling once the cords or the base stations are plugged into the aircraft's' telephone network.

In this example the ground station 24 at the remote location B is linked to the aircraft via the satcomms link and the public switched telephone network PSTN 26. At the remote location B a medical practitioner has an apparatus 28 corresponding to the apparatus on the aircraft for displaying the medical data, and the still images from the camera 9, and two way audio communications for talking to the operator on the aircraft. The medical data and images are viewed within respective windows on the ground display. The medical practitioner at location B preferably has the equipment necessary to transmit all the information received to a third party expert at another location via for example the internet, it being noted that the medical data is transmitted to the remote location according to TCP/IP and FTP which are standard protocols used on the internet.

In a currently preferred embodiment of the system, the ground to air communications links including the communication links within the aircraft have a narrow bandwidth e.g. 2.4 kbs.

As described above, at the response centre B, the medical practitioner may have an apparatus corresponding to the apparatus on the aircraft. In a currently preferred embodiment of the system, the practitioner, at the response centre B has a PC including a store S2 and keys, which may be virtual keys, displayed on the display screen of the PC, corresponding to respective ones of all the keys of the diagnostic apparatus in the aircraft, and a display which replicates the information currently displayed on the display 11 (and on the head mounted display 10 if provided). All actions taken by the users of the diagnostic apparatus on the aircraft, location A, are duplicated on the PC at location B in near "real-time". For this purpose, the PC of the response centre 24 is running software which duplicates all the functions of the software of the PC 104 of the diagnostic apparatus. The PC of the response centre 24 also has additional functionality. Thus the medical practitioner at location B can monitor exactly what occurs at location A. The medical practitioner can intervene when he or she deems it necessary to correct and/or override actions taken at location A. In the currently preferred embodiment of the invention, there are three exceptions I, II, III as follows:

I The camera 9 is a video camera, which as described above, provides a moving image on the display 11 acting as a viewfinder. A still image is selected or "grabbed" when desired and the image is compressed using a known data compression scheme such as JPEG and transmitted via the non-voice communication channel to the response centre. The use of the camera, and the selection of an image to be grabbed is controlled by the operator of the diagnostic apparatus, and not by the response centre. The image is stored at the response centre 24 and the diagnostics apparatus. The still image may be transmitted as a lower resolution image for faster transmission thereof, or as a higher resolution image but transmission time is longer. The camera produces an image of fixed resolution. The transmitted low resolution image is an image having a higher compression ratio than the transmitted high resolution image.

The low resolution image is sufficient to give the remote medical practitioner general information such as age, gender, race and general demeanour of the patient. The low resolution image may also be used to confirm to the medical practitioner at the response centre that the diagnostic apparatus is being correctly used. The high resolution image provides more detailed information.

The response centre controls whether high resolution or low resolution images are produced by sending a signal to the diagnostics apparatus. The default setting is low resolution. That is not controllable by the user of the diagnostic apparatus on the aircraft.

II When the camera 9 is being used to produce moving images, because the bandwidth of the image is too great to be transmitted to the response centre, the PC at the response centre displays, not the video, but a symbol indicating that video is being generated.

III When the ECG array 1 is in use, because the bandwidth of the ECG signals is too great to be transmitted to the response centre 24 in real time the PC at the response centre 24 displays, not the ECG signals as they are generated, but a symbol indicating that they are being generated. The operator of the ECG array controls the selection and transmission of the ECG signal to the response centre.

Context Sensitive Help Screens

The processor 6 of the diagnostic apparatus and the PC at the response centre 24 store identical libraries of context sensitive help screens. The screens preferably display graphical images with a minimum of text illustrating how to perform various tasks. The display of the PC at the response centre 24 duplicates the display of the diagnostic apparatus on the aircraft in near real-time. For that purpose, the diagnostic apparatus transmits to the PC data which identifies the relevant display screen to be displayed, thus minimising the amount of data to be transmitted.

The diagnostic apparatus has a first set of context sensitive help screens which are associated with the various functions of the apparatus and which are automatically displayed in use of the apparatus.

This first set may include for example:
a) screens displayed when the apparatus is initially switched on showing how to connect it to the aircraft's internal telephone system;
b) screens displayed once that is done indicating the next steps to take: e.g. how to initiate use of, and to apply to the patient, the infra-red ear thermometer 2.
c) screens showing how to initiate use of, and to use, the ECG array 1, the combined pulse oximeter and blood pressure monitor 3, and the capnometer 4 respectively.

Such a first set of display screens are automatically displayed in use of the diagnostic apparatus, preferably in response to selection of a function by a control key of the apparatus. Such a first set of display screens is duplicated on the PC at the response centre 24 in near real-time. The response centre 24 may override/correct selection of the function and thus of the display screens. This is done by transmitting to the diagnostics apparatus data including an identifier identifying the image to the displayed, but not the image itself. Even in the event of a break in communication with the response centre 24, the display screens are automatically displayed independently of any or no action taken by the response centre 24.

The display screens of the first set have unique identifiers which are used to identify them.

In accordance with a preferred embodiment of the present invention, a second set of display screens is stored both on the PC at the response centre 24 and in the diagnostic apparatus.

The second set is preferably selectable only by the medical practitioner at the response centre 24; if selected the second set is displayed both at the diagnostic apparatus and at the PC. For that purpose the display screens of the second set have unique identifiers.

The second set provides more detailed instructions on how to perform various tasks. They are intended for use if:
a) a user with no training is required to operate the diagnostic apparatus; or
b) a trained user needs more detailed assistance.

The second set is preferably controlled by the medical practitioner at the response centre 24 to avoid unnecessary confusion of the user of the diagnostic apparatus. Because the second set of display screens are stored in the diagnostic apparatus the PC transmits to it identifiers identifying the screens to be displayed (but not the screens themselves), minimising the amount of data, to be transmitted and thus minimising bandwidth used.

The second set of help screens, controlled by the response centre 24, may comprise two types of screen:
I) screens explaining the use of the apparatus and of the medical sensors 1 to 4;
II) screens explaining medical procedures.

As an example of type I, a help screen or series of help screens explain in detail how to measure blood pressure. A first screen or series of screens identifies the operating key SHIFT BP for actuating blood pressure measurement, the location of the blood pressure measurement cuffs, and the selection of the cuff appropriate to the patient. A second screen or series of screens illustrates how and when to apply the cuff to the patient.

As an example of type II, a series of help screens explain how to treat a severe cut. For example the screens explain in simple steps how to apply a tourniquet.

Especially the screens explaining medical procedures are controlled by the practitioner at the response centre so that such procedures take place only under the supervision of the practitioner. Preferably, the PC at the response centre stores libraries of help screens according to category such as category of medical procedure and category of use of equipment. The practitioner calls up a category and the images (help screens and or camera images) are displayed as small images or "stamps". The practitioner selects a stamp using for example a pointing device and clicks on the selected stamp to cause its identifier to be transmitted to the diagnostic apparatus where the duplicate of the selected image is displayed. Most preferably, the selected stamp is displayed in enlarged form in a viewing window at the response centre so that the practitioner can check it is the correct image and if the image is correct the practitioner clicks on the viewing window to cause the identifier to be transmitted to the diagnostic apparatus.

Image Storage

Still images grabbed from the video camera 9 are stored both in the PC at the response centre 24 and in the diagnostic apparatus. Each image is identified by a unique identifier which is transmitted to the response centre with the still image. The images may be retrieved from storage by the PC at the response centre 24. For example each still image may be displayed on the PC as a reduced size image. When the image is to be retrieved from store the user of the PC uses a pointing device which points to the displayed reduced size image. Any image so retrieved is also displayed at the diagnostic apparatus. For that purpose the PC transmits to the diagnostic apparatus the identifier (and not the image).

Annotations

The medical practitioner at the response centre has facilities for annotating images.

For example, the patient reports pain in their torso. The practitioner asks via the voice channel, for an image of the torso of the patient. The appropriate still image is grabbed from the video and transmitted to the response centre 24. The image may be low resolution or high resolution as selected by the response centre 24. The still image is stored both on the PC at the response centre and in the diagnostic apparatus.

The medical practitioner annotates the still image with for example markings such as an arrow indicating a possible direction of migration of the pain as an aid to diagnosis. The annotation is stored in one file and the image is stored in another separate but associated file in the PC at the response centre 24. The annotation file together with the identifier of the annotated image is transmitted to the diagnostic apparatus. The diagnostic apparatus combines the annotation with the identified still image stored in the diagnostic apparatus and displays combined image and annotation.

The annotation file is small and thus bandwidth is minimised. The annotation file may be compressed before it is transmitted.

The example given above assumes a graphic annotation. Other types of annotation may be used. For example text may be added to an image as an annotation. Furthermore, an annotated image may be re-annotated to provide further information if required.

The annotations may be added to help screens in the same way.

TCP/IP and FTP

Data Communication via the data communication links between the PC at the response centre 24 and the diagnostic apparatus occurs in accordance with the well known TCP/IP standard protocol. Files such as still images, and annotation files are transferred in accordance with the known FTP standard protocol.

Pan/Zoom

Images and help screens are stored both at the response centre 24 and in the diagnostic apparatus on the aircraft. The response centre 24 can select images and help screens for display at the diagnostic apparatus as described above. The response centre can additionally select a portion of an image (or help screen) and enlarge the portion; this is referred to as zoom in the following description. The area to be zoomed may be moved ("panned") across the image. The zooming and panning of images in the diagnostic apparatus is controlled from the response centre 24. In a preferred embodiment this is done in near real-time by transmitting to the diagnostic apparatus variables defining the image, the area to be zoomed and the zoom factor. The variables are transmitted as such and not as files. Thus FTP is not used. Because only variables are used bandwidth is minimised.

Various modifications may be made to the described apparatus. As described above, annotations are transmitted as files using FTP. In a modification, instead of transmitting files, commands and variables defining the annotations and the images to be annotated are transmitted in near real-time without using FTP. As noted above both the PC 104 in the diagnostic apparatus and the PC in the response centre 24 are running the same software. The annotation software defines annotation tools which are further defined as variables. Instead of transmitting an FTP annotation file, commands (such as create, delete annotations) and variables which define the annotation type, and the properties of the annotation such as position, colour etc. are transmitted to the diagnostic apparatus. These variables are interpreted by the diagnostic apparatus to reproduce the annotations at the diagnostic apparatus. Because only commands and variables are transmitted, bandwidth is minimised. A file is provided both at the response centre 24 and at the diagnostic apparatus which logs the variables and the images to which they relate.

The wireless receiver/transmitters 18, 20 may be designed for use with a low earth orbit satellite communications system such as the Iridium™ satellite system. The apparatus could then be used anywhere on the surface of the Earth.

Whilst the present invention has been described by way of example for use on aircraft in relation to humans, it is not limited to that.

The apparatus is useful on other vehicles such as ships and yachts. It may be used on oil rigs or in other locations such as hotels in areas remote from skilled medical assistance.

The apparatus may be used on animals especially mammals.

The invention may be applied to the diagnosis of faults in machines such as aircraft or electronic equipment.

Other uses will be apparent to those skilled in the art.

Although illustrative embodiments of the invention have been described in detail herein with reference to the accompanying drawings, it is to be understood that the invention is not limited to those precise embodiments and thaty various changes and modifications can be effected therein by one skilled in the art without departing from the scope and spirit of the invention as defined by the appended claims.

I claim:

1. A diagnostic system comprising:
   a diagnostic apparatus having at least one diagnostic sensor and a display for displaying an image;
   a complementary apparatus having a display for displaying an image;
   a communication system by which the diagnostic apparatus and the complementary apparatus communicate;
   the diagnostic apparatus and the complementary apparatus being arranged to display the same image;
   the complementary apparatus having means for annotating the said displayed image and for transmitting to the diagnostic apparatus data representing the annotation, the diagnostic apparatus being arranged to display the annotation on the said same image displayed thereat.

2. A system according to claim 1, wherein the diagnostic apparatus and the complementary apparatus each have stores for storing images, the diagnostic apparatus storing a set of a plurality of images and the complementary apparatus storing an identical set.

3. A system according to claim 2, wherein said images have identifiers, and the identifier of an image to be displayed at one of the diagnostic apparatus and the complementary apparatus is transmitted to an other one of the complementary apparatus and the diagnostic apparatus to cause the other one of the complementary apparatus and the diagnostic apparatus to display the same image stored in the store thereof.

4. A system according to claim 2, wherein the said set of images comprises help images illustrating the use of the diagnostic apparatus.

5. A system according to claim 2, comprising a further set of images stored in the stores of the diagnostic apparatus and the complementary apparatus, the images of the further set being displayable at the diagnostic apparatus only in response to a command produced at the complementary apparatus.

6. A system according to claim 5, wherein the images of the further set illustrate medical procedures.

7. A system according to claim 2, wherein the diagnostic apparatus has a camera for creating images, images created by the camera being transmitted to the complementary apparatus by the communication system and stored in the said stores of the diagnostic apparatus and the complementary apparatus.

8. A system according to claim 1, wherein the said data representing an annotation comprises a file containing information representing the annotation, the diagnostic apparatus being arranged to display the annotation represented in the file.

9. A system according to claim 1, wherein the said data representing an annotation comprises commands and variables defining the annotation, the diagnostic apparatus being arranged to recreate the annotation therefrom.

10. A diagnostic apparatus for use with a complementary apparatus having a display for displaying an image, the diagnostic apparatus having:
- at least one diagnostic sensor and a display for displaying an image;
- a communication system by which the diagnostic apparatus and the complementary apparatus communicate;
- the diagnostic apparatus and the complementary apparatus being arranged to display the same image;
- the diagnostic apparatus being arranged to receive, from the complementary apparatus, via the communication system, data representing an annotation of the image and to display the annotation on the image displayed thereat.

11. Apparatus according to claim 10, further comprising a camera for creating images, the apparatus being arranged to store images created by the camera and to transmit the created images to the complementary apparatus via the communication system for storage in the store of the complementary apparatus.

12. Apparatus according to claim 10, wherein the data representing an annotation comprises a file containing information representing the annotation, the diagnostic apparatus being arranged to display the annotation represented in the file.

13. Apparatus according to claim 10, wherein the said data representing an annotation comprises commands and variables defining the annotation, the diagnostic apparatus being arranged to recreate the annotation therefrom.

14. A diagnostic system comprising:
- a diagnostic apparatus having at least one diagnostic sensor and a display for displaying an image;
- a complementary apparatus having a display for displaying an image;
- a communication system by which the diagnostic apparatus and the complementary apparatus communicate;
- the diagnostic apparatus and the complementary apparatus being arranged to display the same image;
- wherein the diagnostic apparatus and the complementary apparatus each have stores for storing images, the diagnostic apparatus storing a set of a plurality of images and the complementary apparatus storing an identical set and wherein the said images have identifiers, and the identifier of an image to be displayed at one of the diagnostic apparatus and the complementary apparatus is transmitted to an other one of the complementary apparatus and the diagnostic apparatus to cause the other one of the complementary apparatus and the diagnostic apparatus to display the same image stored in the store thereof.

15. A system according to claim 14, wherein the said set of images comprises help images illustrating the use of the apparatus.

16. A system according to claim 14, comprising a further set of images stored in the stores of the diagnostic apparatus and the complementary apparatus, the images of the further set being displayable at the diagnostic apparatus only in response to a command produced at the complementary apparatus.

17. A system according to claim 16, wherein the images of the further set illustrate medical procedures.

18. A system according to claim 14, wherein the diagnostic apparatus has a camera for creating images, images created by the camera being transmitted to the complementary apparatus by the communication system and stored in the said stores of the diagnostic apparatus and the complementary apparatus.

19. A diagnostic apparatus for use with a complementary apparatus having a display for displaying an image and a store for storing images to be displayed, the diagnostic apparatus having: at least one diagnostic sensor; a display for displaying an image; a communication system by which the diagnostic apparatus and the complementary apparatus communicate; and a store for storing images, the diagnostic apparatus storing a set of a plurality of images, which images are identical to images stored at the complementary apparatus;

the diagnostic apparatus being arranged to receive from the complementary apparatus and/or to transmit to the complementary apparatus, via the communication system an identifier of an image to be displayed at one of the diagnostic apparatus and the complementary apparatus to cause it to display the identified image stored in the store thereof.

20. An apparatus according to claim 19, wherein the said set of images comprises help images illustrating the use of the diagnostic apparatus.

21. An apparatus according to claim 19, comprising a further set of images stored in the stores of the diagnostic apparatus and the complementary apparatus, the images of the further set being displayable at the diagnostic apparatus only in response to a command produced at the complementary apparatus.

22. An apparatus according to claim 21, wherein the images of the further set illustrate medical procedures.

23. An apparatus according to claim 19, wherein the diagnostic apparatus has a camera for creating images, images created by the camera being transmitted to the complementary apparatus by the communication system and stored in the said stores of the diagnostic apparatus and the complementary apparatus.

24. Diagnostic apparatus comprising:
- means for sensing diagnostic data; communication means for transmitting the sensed data to a remote location and for receiving control data from the remote location;
- display means;
- processing means to which the sensing means, communication means and display means are connected to form an integrated system, the processing means being arranged to:
  - a) control the sensing means;
  - b) process the sensed data; and
  - c) control the communication means;
- the processing means storing a set of images each image having a unique identifier, the processing means being responsive to a command from the remote location to select and display a stored image identified by the command.

25. Apparatus according to claim 24, comprising a camera for producing still images, the said stored images including images produced by the camera.

26. Apparatus according to claim 25, wherein the processing means causes each still image produced by the camera to be transmitted by the communication means to the remote location.

27. Apparatus according to claim 24, wherein the stored images include images representing context sensitive instructions.

28. Apparatus according to claim 24, wherein the processing means is responsive to an image annotation, together with the identifier of the image to be annotated, received from the remote location to combine the annotation with the identified image stored by the processing means and to display the annotated image.

29. Apparatus according to claim 24, wherein the stored images include images selectable and displayable only in response to a command received from the remote location.

30. A diagnostic system comprising:

diagnostic apparatus according to claim 24; and a complementary apparatus at the remote location comprising communication means for receiving sensed data from the diagnostic apparatus, a display and a processor, the processor of the device storing a set of images identical to the said set of images stored by the said processing means.

31. A system according to claim 30, wherein the complementary apparatus is arranged to: select an image for annotation; annotate the image; and transmit the annotation, but not the image, to the diagnostic apparatus together with the identifier of the selected image.

32. A system according to claim 30, wherein the complementary apparatus is arranged to select a stored image and to transmit to the diagnostic apparatus the identifier of the image and a command causing the diagnostic apparatus to display the identified image stored in the diagnostic apparatus.

33. A system according to claim 30, wherein the said complementary apparatus is arranged to display images identical to those displayed by the diagnostic apparatus.

34. A diagnostic system comprising:

a diagnostic apparatus having at least one diagnostic sensor and a display for displaying an image;

a complementary apparatus having a display for displaying an image;

a communication system by which the diagnostic apparatus and the complementary apparatus communicate;

the diagnostic apparatus being arranged to perform a predetermined plurality of actions;

the diagnostic apparatus and the complementary apparatus being arranged so that the complementary apparatus replicates the said actions.

35. A diagnostic system comprising:

a diagnostic apparatus having at least one diagnostic sensor and a display for displaying an image;

a complementary apparatus having a display for displaying an image;

a communication system by which the diagnostic apparatus and this complementary apparatus communicate;

the diagnostic apparatus and the complementary apparatus being arranged to display the same image;

the complementary apparatus having an annotator operable to annotate the said displayed image and to transmit to the diagnostic apparatus data representing the annotation without the image, the diagnostic apparatus having a combiner operable to combine the said annotation with the said same image displayed thereat.

36. A complementary apparatus for use with a diagnostic apparatus having at least one diagnostic sensor, the diagnostic apparatus having a display for displaying an image, the complementary apparatus having a display for displaying an image, the diagnostic and complementary apparatus being arranged to display the same image including data from the at least one diagnostic sensor when the data is displayed by the diagnostic apparatus, the complementary apparatus further having a communication interface via which the diagnostic apparatus and the complementary apparatus communicate; the complementary apparatus being operable to annotate an image displayed on the complementary apparatus and to transmit, via the communication device, data representing the annotation of the image without the image, to the diagnostic apparatus for display of the annotation on the same image displayed at the diagnostic apparatus.

* * * * *